United States Patent
Brzychczy-Wloch et al.

(10) Patent No.: US 12,153,047 B2
(45) Date of Patent: Nov. 26, 2024

(54) DIAGNOSTIC TEST (71) Applicants: UNIWERSYTET JAGIELLONSKI, Cracow (PL); INSTYTUT IMMUNOLOGII I TERAPII DOSWIADCZALNEJ POLSKIEJ AKADEMII NAUK, Wroclaw (PL)

(72) Inventors: Monika Brzychczy-Wloch, Cracow (PL); Anna Dobrut, Cracow (PL); Sabina Gorska, Wroclaw (PL); Ewa Brzozowska, Wroclaw (PL); Andrzej Gamian, Wroclaw (PL)

(73) Assignees: UNIWERSYTET JAGIELLONSKI, Cracow (PL); INSTYTUT IMMUNOLOGII I TERAPII DOSWIADCZALNEJ POLSKIEJ AKADEMII NAUK, Wroclaw (PL)

( * ) Notice: Subject to any disclaimer, the term of this patent is extended or adjusted under 35 U.S.C. 154(b) by 1153 days.

(21) Appl. No.: 16/960,844

(22) PCT Filed: Jan. 9, 2019

(86) PCT No.: PCT/PL2019/050002
§ 371 (c)(1),
(2) Date: Jul. 8, 2020

(87) PCT Pub. No.: WO2019/139494
PCT Pub. Date: Jul. 18, 2019

(65) Prior Publication Data
US 2021/0033607 A1    Feb. 4, 2021

(30) Foreign Application Priority Data
Jan. 9, 2018   (PL) .......................... 424214

(51) Int. Cl.
*G01N 31/00* (2006.01)
*C07K 14/315* (2006.01)
*G01N 33/53* (2006.01)
*G01N 33/569* (2006.01)

(52) U.S. Cl.
CPC ..... *G01N 33/56944* (2013.01); *C07K 14/315* (2013.01); *G01N 2333/315* (2013.01)

(58) Field of Classification Search
None
See application file for complete search history.

(56) References Cited

U.S. PATENT DOCUMENTS 10,048,263 B2 * 8/2018 Brzychczy-Wloch .......... C07K 14/315
10,706,955 B2 * 7/2020 Bremel .................. G16B 20/00

FOREIGN PATENT DOCUMENTS

| JP | 2010/263839 A | 11/2010 | | |
|---|---|---|---|---|
| WO | 88/06591 A1 | 9/1988 | | |
| WO | 01/16174 A2 | 3/2001 | | |
| WO | 02/092818 A2 | 11/2002 | | |
| WO | WO-2006069200 A2 * | 6/2006 | .......... | C07K 14/315 |
| WO | 2011/119484 A1 | 9/2011 | | |
| WO | WO-2014209142 A1 * | 12/2014 | .......... | C07K 14/315 |

OTHER PUBLICATIONS

Maggio (Immunoenzyme technique I, CRC press 1980, pp. 186-187). (Year: 1980).*
Database UniProtKB [Online]; Feb. 15, 2017 (Feb. 15, 2017) "Inosine-5'-monophosphate dehydrogenase", retrieved from EBI accession No. Uniprot: A0A1J7W9Q9, database accession No. A0A1J7W9Q9.
Database Gen Bank [Online]; Aug. 30, 2005 (Aug. 30, 2005) "60 kDa chaperonin (Protein Cpn60) (groEL protein) [*Streptococcus agalactiae* 18RS21]", retrieved from NCBI Blast: Protein Sequence, database accession No. EAO62388.1.
M.Brzychczy-Wloch et al: "Identification of high immunoreactive proteins from *Streptococcus agalactiae* isolates recognized by human serum antibodies", FEMS Microbiology Letters; Oct. 24, 2013 {Oct. 23, 2013), vol. 349, No. 1, pp. 61-70, doi.org/10.1111/1574-6968.12292.
K. Fluegge et al: "Identification and immunoreactivity of proteins released from *Streptococcus agalactiae*", European Journal of Clinical Microbiology & Infectious Diseases; vol. 23, No. 11, Nov. 1, 2004 (Nov. 1, 2004), pp. 818-824, doi:10.1007/s10096-004-1229-y.
Written Opinion of ISA, PCT/PL2019/050002, May 8, 2019.
Search Report of ISA, PCT/PL2019/050002, May 8, 2019.
Uniprot Database ID: W1UMS6_9STRE. (Dec. 20, 2017). "Fragment of Inositol 5'-monophosphate dehydrogenase from *Streptocossus*.".
Morrison and Weiss. Combinatorial alannine-scanning. Combinatorial Chemistry, 2001, 5(3), 302-307.
Brzychczy-Wloch et al. Identification of high immunoreactive proteins from *Steptococcus agalactiae* isolates recognized by human serum antibodies. FEMS Microbiology, 2013, 349, 61-70.
Uniprot Database ID: UPI000A829624. (Mar. 19, 2014). "Candidatus Yonathbacteria bacterium.".
Uniprot Database ID: L1JBN9_GUITH. (Nov. 22, 2017). "Uncharacterized protein from *Guillardia theta*.".

* cited by examiner

*Primary Examiner* — Lisa V Cook
(74) *Attorney, Agent, or Firm* — Arrigo, Lee, Guttman & Mouta-Bellum LLP (57) ABSTRACT

The method according to the invention enables the confirmation of infections/carriage caused by *Streptococcus agalactiae* bacterial species. The method employs a specific reaction of selected epitopes that are part of immunoreactive proteins of clinical isolates of *Streptococcus agalactiae* with antibodies present in the serum.

8 Claims, 6 Drawing Sheets
Specification includes a Sequence Listing.

Fig. 1

Amino acid sequences of immunoreactive proteins of *S. agalactiae*.

Sekw. NRID5

MSNWDTKFLKKGFTFDDVLLIPAESHVLPNEVDMNTKLADNLTLNIPIITAAMDTVT
DSKMAIAIARAGGLGIIHKNMSIVDQAEEVRKVKRSENGVIIDPFFLTPDNTVSEAEEL
MQNYRISGVPIVETLENRKLVGIITNRDMRFISDYKQLISEHMTSQNLVTAPIGTDLET
AERILHEHRIEKLPLVDDEGRLSGLITIKDIEKVIEFPKAAKDEFGRLLVAGAVGVTSD
TFERAEALFEAGADAIVIDTAHGHSAGVLRKIAEIRAHFPNRTLIAGNIATAEGARALY
DAGVDVVKVGIGPGSICTTRVVAGVGVPQITAIYDAAAVAREYGKTIIADGGIKYSGD
IVKALAAGGNAVMLGSMFAGTDEAPGETEIFQGRKFKTYRGMGSIAAMKKGSSDRY
FQGSVNEANKLVPEGIEGRVAYKGSVADIVFQMLGGIRSGMGYVGAANIKELHDNA
QFVEMSGAGLKESHPHDVQITNEAPNYSVH

Sekw. NRID6

MAKDIKFSADARSAMVRGVDILADTVKVTLGPKGRNVVLEKAFGSPLITNDGVTIAK
EIELEDHFENMGAKLVSEVASKTNDIAGDGTTTATVLTQAIVREGLKNVTAGANPIGI
RRGIETAVSAAVEELKEIAQPVSGKEAIAQVAAVSSRSEKVGEYISEAMERVGNDGVI
TIEESRGMETELEVVEGMQFDRGYLSQYMVTDNEKMVSELENPYILITDKKISNIQEIL
PLLEEVLKTNRPLLIIADDVDGEALPTLVLNKIRGTFNVVAVKAPGFGDRRKAMLEDI
AILTGGTVVTEDLGLDLKDATMQVLGQSAKVTVDKDSTVIVEGAGDSSAIANRVAII
KSQMEATTSDFDREKLQERLAKLAGGVAVIKVGAATETELKEMKLRIEDALNATRA
AVEEGIVSGGGTALVNVIEKVAALKLNGDEETGRNIVLRALEEPVRQIAYNAGYEGS
VIIERLKQSEIGTGFNAABGEWVDMVTTGIIDPVKVTRSALQNAASVASLILTTEAVV
ANKPEPEAPTAPAMDPSMMGGF

Fig. 2

Photo example from Western blot analysis using three strains: S55 (1736/08), S57 (13793/08), D129. The following sera from umbilical cord blood were used to check immunogenicity: A) 3/KP (inactivated), B) 1/KP, C) 6/KP. Immunoreactive proteins were NRID5 and NRID6 with weights of about 55 kDa.

Fig. 3

Specificity of polypeptide core epitopes of S. *agalactiae* with a mix of GBS-positive sera and a mix of GBS-negative sera.

Fig. 4

Example of reactivity of peptides modified by alanine substitution for a derivative of the core epitope MVTTGIIDPVKV (Ep9) of the NRID6 protein.

Example of specificity of a derivative of the Ep4 epitope of the NRID4 protein assessed in the ELISA test against selected sera: 6 / KP - serum from a patient with GBS carrier, GBS 2a - serum from a patient with GBS infection, 13 / KP - serum from GBS-negative patient (negative control); GAS - serum from a patient with S. pyogenes infection (negative control). Fig. 5A: results obtained for IgG antibodies; Fig. 5B: results for IgM antibodies.

Fig. 6

An example of an ELISA test comparing the protein reactivity of an elongation factor Tu (EF-Tu; NRID4 protein) and a derivative of one of its epitopes (Ep4) with the sequence KPGSINPHTKF. Legend: GBS + - serum from a patient with GBS carrier, GBS- - serum from a non-GBS carrier (negative control).

SEQUENCE LISTING

<160> NUMBER OF SEQ ID NOS: 27

<210> SEQ ID NO 1
<211> LENGTH: 493
<212> TYPE: PRT
<213> ORGANISM: Streptococcus agalactiae

<400> SEQUENCE: 1

Met Ser Asn Trp Asp Thr Lys Phe Leu Lys Lys Gly Phe Thr Phe Asp
1               5                   10                  15

Asp Val Leu Leu Ile Pro Ala Glu Ser His Val Leu Pro Asn Glu Val
            20                  25                  30

Asp Met Asn Thr Lys Leu Ala Asp Asn Leu Thr Leu Asn Ile Pro Ile
        35                  40                  45

Ile Thr Ala Ala Met Asp Thr Val Thr Asp Ser Lys Met Ala Ile Ala
50                  55                  60

Ile Ala Arg Ala Gly Gly Leu Gly Ile Ile His Lys Asn Met Ser Ile
65                  70                  75                  80

Val Asp Gln Ala Glu Glu Val Arg Lys Val Lys Arg Ser Glu Asn Gly
            85                  90                  95

Val Ile Ile Asp Pro Phe Phe Leu Thr Pro Asp Asn Thr Val Ser Glu
        100                 105                 110

Ala Glu Glu Leu Met Gln Asn Tyr Arg Ile Ser Gly Val Pro Ile Val
    115                 120                 125

Glu Thr Leu Glu Asn Arg Lys Leu Val Gly Ile Ile Thr Asn Arg Asp
130                 135                 140

Met Arg Phe Ile Ser Asp Tyr Lys Gln Leu Ile Ser Glu His Met Thr
145                 150                 155                 160

Ser Gln Asn Leu Val Thr Ala Pro Ile Gly Thr Asp Leu Glu Thr Ala
            165                 170                 175

Glu Arg Ile Leu His Glu His Arg Ile Glu Lys Leu Pro Leu Val Asp
        180                 185                 190

Asp Glu Gly Arg Leu Ser Gly Leu Ile Thr Ile Lys Asp Ile Glu Lys
    195                 200                 205

Val Ile Glu Phe Pro Lys Ala Ala Lys Asp Glu Phe Gly Arg Leu Leu
210                 215                 220

```
Val Ala Gly Ala Val Gly Val Thr Ser Asp Thr Phe Glu Arg Ala Glu
225                 230                 235                 240

Ala Leu Phe Glu Ala Gly Ala Asp Ala Ile Val Ile Asp Thr Ala His
            245                 250                 255

Gly His Ser Ala Gly Val Leu Arg Lys Ile Ala Glu Ile Arg Ala His
        260                 265                 270

Phe Pro Asn Arg Thr Leu Ile Ala Gly Asn Ile Ala Thr Ala Glu Gly
    275                 280                 285

Ala Arg Ala Leu Tyr Asp Ala Gly Val Asp Val Lys Val Gly Ile
290                 295                 300

Gly Pro Gly Ser Ile Cys Thr Thr Arg Val Val Ala Gly Val Gly Val
305                 310                 315                 320

Pro Gln Ile Thr Ala Ile Tyr Asp Ala Ala Val Ala Arg Glu Tyr
                325                 330                 335

Gly Lys Thr Ile Ile Ala Asp Gly Gly Ile Lys Tyr Ser Gly Asp Ile
                340                 345                 350

Val Lys Ala Leu Ala Ala Gly Gly Asn Ala Val Met Leu Gly Ser Met
            355                 360                 365

Phe Ala Gly Thr Asp Glu Ala Pro Gly Glu Thr Glu Ile Phe Gln Gly
    370                 375                 380

Arg Lys Phe Lys Thr Tyr Arg Gly Met Gly Ser Ile Ala Ala Met Lys
385                 390                 395                 400

Lys Gly Ser Ser Asp Arg Tyr Phe Gln Gly Ser Val Asn Glu Ala Asn
                405                 410                 415

Lys Leu Val Pro Glu Gly Ile Glu Gly Arg Val Ala Tyr Lys Gly Ser
            420                 425                 430

Val Ala Asp Ile Val Phe Gln Met Leu Gly Gly Ile Arg Ser Gly Met
            435                 440                 445

Gly Tyr Val Gly Ala Ala Asn Ile Lys Glu Leu His Asp Asn Ala Gln
    450                 455                 460

Phe Val Glu Met Ser Gly Ala Gly Leu Lys Glu Ser His Pro His Asp
465                 470                 475                 480

Val Gln Ile Thr Asn Glu Ala Pro Asn Tyr Ser Val His
                485                 490

<210> SEQ ID NO 2
<211> LENGTH: 540
<212> TYPE: PRT
<213> ORGANISM: Streptococcus agalactiae

<400> SEQUENCE: 2

Met Ala Lys Asp Ile Lys Phe Ser Ala Asp Ala Arg Ser Ala Met Val
1               5                   10                  15

Arg Gly Val Asp Ile Leu Ala Asp Thr Val Lys Val Thr Leu Gly Pro
                20                  25                  30

Lys Gly Arg Asn Val Val Leu Glu Lys Ala Phe Gly Ser Pro Leu Ile
            35                  40                  45

Thr Asn Asp Gly Val Thr Ile Ala Lys Glu Ile Glu Leu Glu Asp His
    50                  55                  60

Phe Glu Asn Met Gly Ala Lys Leu Val Ser Glu Val Ala Ser Lys Thr
65                  70                  75                  80

Asn Asp Ile Ala Gly Asp Gly Thr Thr Thr Ala Thr Val Leu Thr Gln
                85                  90                  95

Ala Ile Val Arg Glu Gly Leu Lys Asn Val Thr Ala Gly Ala Asn Pro
                100                 105                 110
```

```
Ile Gly Ile Arg Arg Gly Ile Glu Thr Ala Val Ser Ala Ala Val Glu
        115                 120                 125
Glu Leu Lys Glu Ile Ala Gln Pro Val Ser Gly Lys Glu Ala Ile Ala
        130                 135                 140
Gln Val Ala Val Ser Ser Arg Ser Glu Lys Val Gly Glu Tyr Ile
145                 150                 155                 160
Ser Glu Ala Met Glu Arg Val Gly Asn Asp Gly Val Ile Thr Ile Glu
                165                 170                 175
Glu Ser Arg Gly Met Glu Thr Glu Leu Glu Val Val Glu Gly Met Gln
            180                 185                 190
Phe Asp Arg Gly Tyr Leu Ser Gln Tyr Met Val Thr Asp Asn Glu Lys
            195                 200                 205
Met Val Ser Glu Leu Glu Asn Pro Tyr Ile Leu Ile Thr Asp Lys Lys
        210                 215                 220
Ile Ser Asn Ile Gln Glu Ile Leu Pro Leu Leu Glu Glu Val Leu Lys
225                 230                 235                 240
Thr Asn Arg Pro Leu Leu Ile Ile Ala Asp Asp Val Asp Gly Glu Ala
                245                 250                 255
Leu Pro Thr Leu Val Leu Asn Lys Ile Arg Gly Thr Phe Asn Val Val
            260                 265                 270
Ala Val Lys Ala Pro Gly Phe Gly Asp Arg Arg Lys Ala Met Leu Glu
        275                 280                 285
Asp Ile Ala Ile Leu Thr Gly Gly Thr Val Val Thr Glu Asp Leu Gly
        290                 295                 300
Leu Asp Leu Lys Asp Ala Thr Met Gln Val Leu Gly Gln Ser Ala Lys
305                 310                 315                 320
Val Thr Val Asp Lys Asp Ser Thr Val Ile Val Glu Gly Ala Gly Asp
                325                 330                 335
Ser Ser Ala Ile Ala Asn Arg Val Ala Ile Ile Lys Ser Gln Met Glu
            340                 345                 350
Ala Thr Thr Ser Asp Phe Asp Arg Glu Lys Leu Gln Glu Arg Leu Ala
        355                 360                 365
Lys Leu Ala Gly Gly Val Ala Val Ile Lys Val Gly Ala Ala Thr Glu
        370                 375                 380
Thr Glu Leu Lys Glu Met Lys Leu Arg Ile Glu Asp Ala Leu Asn Ala
385                 390                 395                 400
Thr Arg Ala Ala Val Glu Glu Gly Ile Val Ser Gly Gly Thr Ala
                405                 410                 415
Leu Val Asn Val Ile Glu Lys Val Ala Ala Leu Lys Leu Asn Gly Asp
            420                 425                 430
Glu Glu Thr Gly Arg Asn Ile Val Leu Arg Ala Leu Glu Glu Pro Val
        435                 440                 445
Arg Gln Ile Ala Tyr Asn Ala Gly Tyr Glu Gly Ser Val Ile Ile Glu
        450                 455                 460
Arg Leu Lys Gln Ser Glu Ile Gly Thr Gly Phe Asn Ala Ala Asx Gly
465                 470                 475                 480
Glu Trp Val Asp Met Val Thr Thr Gly Ile Ile Asp Pro Val Lys Val
                485                 490                 495
Thr Arg Ser Ala Leu Gln Asn Ala Ala Ser Val Ala Ser Leu Ile Leu
            500                 505                 510
Thr Thr Glu Ala Val Val Ala Asn Lys Pro Glu Pro Glu Ala Pro Thr
        515                 520                 525
```

```
Ala Pro Ala Met Asp Pro Ser Met Met Gly Gly Phe
    530                 535                 540
```

<210> SEQ ID NO 3
<211> LENGTH: 16
<212> TYPE: PRT
<213> ORGANISM: Streptococcus agalactiae

<400> SEQUENCE: 3

```
Arg Ala Ala Ala Asp Tyr Leu Glu Val Pro Leu Tyr Ser Tyr Leu Gly
1               5                   10                  15
```

<210> SEQ ID NO 4
<211> LENGTH: 14
<212> TYPE: PRT
<213> ORGANISM: Streptococcus agalactiae

<400> SEQUENCE: 4

```
Asp Arg Ala Met Ile Ala Leu Asp Gly Thr Pro Asn Lys Gly
1               5                   10
```

<210> SEQ ID NO 5
<211> LENGTH: 14
<212> TYPE: PRT
<213> ORGANISM: Streptococcus agalactiae

<400> SEQUENCE: 5

```
Leu Thr Ala Ala Ile Thr Thr Val Leu Ala Arg Arg Leu Pro
1               5                   10
```

<210> SEQ ID NO 6
<211> LENGTH: 16
<212> TYPE: PRT
<213> ORGANISM: Streptococcus agalactiae

<400> SEQUENCE: 6

```
Gly Gln Val Leu Ala Lys Pro Gly Ser Ile Asn Pro His Thr Lys Phe
1               5                   10                  15
```

<210> SEQ ID NO 7
<211> LENGTH: 15
<212> TYPE: PRT
<213> ORGANISM: Streptococcus agalactiae

<400> SEQUENCE: 7

```
Val Val Lys Val Gly Ile Gly Pro Gly Ser Ile Cys Thr Thr Arg
1               5                   10                  15
```

<210> SEQ ID NO 8
<211> LENGTH: 10
<212> TYPE: PRT
<213> ORGANISM: Streptococcus agalactiae

<400> SEQUENCE: 8

```
Gln Gly Arg Lys Phe Lys Thr Tyr Arg Gly
1               5                   10
```

<210> SEQ ID NO 9
<211> LENGTH: 10
<212> TYPE: PRT
<213> ORGANISM: Streptococcus agalactiae

<400> SEQUENCE: 9

```
Lys Ala Phe Gly Ser Pro Leu Ile Thr Asn
1               5                   10
```

```
<210> SEQ ID NO 10
<211> LENGTH: 12
<212> TYPE: PRT
<213> ORGANISM: Streptococcus agalactiae

<400> SEQUENCE: 10

Ala Gly Gly Val Ala Val Ile Lys Val Gly Ala Ala
1               5                   10

<210> SEQ ID NO 11
<211> LENGTH: 12
<212> TYPE: PRT
<213> ORGANISM: Streptococcus agalactiae

<400> SEQUENCE: 11

Met Val Thr Thr Gly Ile Ile Asp Pro Val Lys Val
1               5                   10

<210> SEQ ID NO 12
<211> LENGTH: 10
<212> TYPE: PRT
<213> ORGANISM: Streptococcus agalactiae

<400> SEQUENCE: 12

Lys Leu Gln Glu Arg Leu Ala Lys Leu Ala
1               5                   10

<210> SEQ ID NO 13
<211> LENGTH: 13
<212> TYPE: PRT
<213> ORGANISM: Streptococcus agalactiae

<400> SEQUENCE: 13

Ala Ala Thr Glu Thr Glu Leu Lys Glu Met Lys Leu Arg
1               5                   10

<210> SEQ ID NO 14
<211> LENGTH: 10
<212> TYPE: PRT
<213> ORGANISM: Streptococcus agalactiae

<400> SEQUENCE: 14

Lys Val Thr Arg Ser Ala Leu Gln Asn Ala
1               5                   10

<210> SEQ ID NO 15
<211> LENGTH: 15
<212> TYPE: PRT
<213> ORGANISM: Streptococcus agalactiae

<400> SEQUENCE: 15

Leu Gln Asn Ala Ala Ser Val Ala Ser Leu Ile Leu Thr Thr Glu
1               5                   10                  15

<210> SEQ ID NO 16
<211> LENGTH: 11
<212> TYPE: PRT
<213> ORGANISM: Artificial Sequence
<220> FEATURE:
<223> OTHER INFORMATION: epitope derivative

<400> SEQUENCE: 16

Met Val Thr Thr Gly Ile Ile Asp Pro Val Ala
1               5                   10
```

<210> SEQ ID NO 17
<211> LENGTH: 11
<212> TYPE: PRT
<213> ORGANISM: Artificial Sequence
<220> FEATURE:
<223> OTHER INFORMATION: epitope derivative

<400> SEQUENCE: 17

Met Val Thr Thr Gly Ile Ile Asp Pro Ala Lys
1               5                   10

<210> SEQ ID NO 18
<211> LENGTH: 11
<212> TYPE: PRT
<213> ORGANISM: Artificial Sequence
<220> FEATURE:
<223> OTHER INFORMATION: epitope derivative

<400> SEQUENCE: 18

Met Val Thr Thr Gly Ile Ile Asp Ala Val Lys
1               5                   10

<210> SEQ ID NO 19
<211> LENGTH: 11
<212> TYPE: PRT
<213> ORGANISM: Artificial Sequence
<220> FEATURE:
<223> OTHER INFORMATION: epitope derivative

<400> SEQUENCE: 19

Met Val Thr Thr Gly Ile Ile Ala Pro Val Lys
1               5                   10

<210> SEQ ID NO 20
<211> LENGTH: 11
<212> TYPE: PRT
<213> ORGANISM: Artificial Sequence
<220> FEATURE:
<223> OTHER INFORMATION: epitope derivative

<400> SEQUENCE: 20

Met Val Thr Thr Gly Ile Ala Asp Pro Val Lys
1               5                   10

<210> SEQ ID NO 21
<211> LENGTH: 11
<212> TYPE: PRT
<213> ORGANISM: Artificial Sequence
<220> FEATURE:
<223> OTHER INFORMATION: epitope derivative

<400> SEQUENCE: 21

Met Val Thr Thr Gly Ala Ile Asp Pro Val Lys
1               5                   10

<210> SEQ ID NO 22
<211> LENGTH: 11
<212> TYPE: PRT
<213> ORGANISM: Artificial Sequence
<220> FEATURE:
<223> OTHER INFORMATION: epitope derivative

<400> SEQUENCE: 22

Met Val Thr Thr Ala Ile Ile Asp Pro Val Lys
1               5                   10

<210> SEQ ID NO 23
<211> LENGTH: 11
<212> TYPE: PRT
<213> ORGANISM: Artificial Sequence
<220> FEATURE:
<223> OTHER INFORMATION: epitope derivative

<400> SEQUENCE: 23

Met Val Thr Ala Gly Ile Ile Asp Pro Val Lys
1               5                   10

<210> SEQ ID NO 24
<211> LENGTH: 11
<212> TYPE: PRT
<213> ORGANISM: Artificial Sequence
<220> FEATURE:
<223> OTHER INFORMATION: epitope derivative

<400> SEQUENCE: 24

Met Val Ala Thr Gly Ile Ile Asp Pro Val Lys
1               5                   10

<210> SEQ ID NO 25
<211> LENGTH: 11
<212> TYPE: PRT
<213> ORGANISM: Artificial Sequence
<220> FEATURE:
<223> OTHER INFORMATION: pochodna epitopu

<400> SEQUENCE: 25

Met Ala Thr Thr Gly Ile Ile Asp Pro Val Lys
1               5                   10

<210> SEQ ID NO 26
<211> LENGTH: 11
<212> TYPE: PRT
<213> ORGANISM: Artificial Sequence
<220> FEATURE:
<223> OTHER INFORMATION: epitope derivative

<400> SEQUENCE: 26

Ala Val Thr Thr Gly Ile Ile Asp Pro Val Lys
1               5                   10

<210> SEQ ID NO 27
<211> LENGTH: 11
<212> TYPE: PRT
<213> ORGANISM: Artificial Sequence
<220> FEATURE:
<223> OTHER INFORMATION: epitope derivative

<400> SEQUENCE: 27

Met Val Thr Thr Gly Ile Ile Asp Pro Val Lys
1               5                   10

DIAGNOSTIC TEST

The subject of the invention is a diagnostic test for the detection, in a highly specific and sensitive manner, of *Streptococcus agalactiae* (Group B *Streptococcus*; GBS) infections and carriage in humans. The diagnostic test employs markers, hereinafter referred to as epitopes, which are recognized in the immunoenzymatic test by different classes (IgG, IgM, and IgA) of human antibodies present in the serum. In particular, the invention concerns a diagnostic test enabling the confirmation of *Streptococcus agalactiae* infections in pregnant women, which makes use of a specific reaction of immunoreactive proteins obtained from *Streptococcus agalactiae* clinical isolates with antibodies present in the serum of patients.

*Streptococcus agalactiae*, of serological group B (group B *streptococcus*; GBS), can colonize the lower gastrointestinal tract, anus and vagina without any symptoms of infection. It was confirmed that GBS is present in the vagina or rectum in about 10-30% of pregnant women. This colonization can be transient, chronic, or intermittent. However, the presence of group B streptococci in the vagina of pregnant women is a vital risk factor for neonatal infection. Intrauterine infection may develop in the course of pregnancy, by ascension, as well as due to aspiration of infected amniotic fluid by the fetus. This may result in intrauterine death, neonatal pneumonia, or sepsis. Colonization of a newborn can also occur during the delivery but, in these cases, only asymptomatic colonization of the skin and mucous membranes is more frequently observed and not infection development. Rapid diagnostics for infections caused by GBS is essential to have the possibility of using targeted antibiotic therapy. However, the market currently lacks rapid diagnostic tests enabling the confirmation of infections caused by *Streptococcus agalactiae*.

The Polish patent application no. P.404498 presents sequences of four proteins (NRID1, NRID2, NRID3, NRID4) of *Streptococcus agalactiae* strains causing infections in humans, which were highly immunoreactive with sera of people who underwent GBS infection and carriers of these bacteria. Lack of similar reactivity was demonstrated in the case of sera from non-infected people and *S. agalactiae* non-carriers.

The application no. EP20070825757 involves polypeptide derivatives of protein epitopes of *Streptococcus agalactiae*—GBS80 and the application of the epitope mentioned for diagnostic purposes. The diagnostics concerns infections in animals. The polypeptide epitope belongs to the protein sequence called cell wall surface anchor protein in GBS. These are polypeptide epitopes different from those encompassed by this application. Another type of epitopes, which may be a diagnostic tool for GBS infections and which differ from those described in this application, was included in the application no. PCT/IB2002/003059.

The objective of the invention is to provide new methods for the detection of infections caused by *Streptococcus agalactiae* and measures that can be employed to implement such methods.

The subject of the invention is a protein comprising an amino acid sequence selected from Seq. No. 1-2 and epitopes contained in them.

Another subject of the invention is an epitope specific for infectious *Streptococcus agalactiae* having an amino acid sequence selected from Seq. No. 3-15 and its derivatives in which at least one of the amino acids was removed or replaced with another amino acid, preferably selected from Ala or Gly, or its biotinylated form. Preferably, the epitope according to the invention is characterized by the fact that it has an amino acid sequence that is a derivative of a sequence selected from Seq. No. 3-15, in which at least one of the amino acids was removed or replaced with another amino acid, preferably selected from Ala or Gly, or its biotinylated form. Preferably, the derivative of the epitope according to the invention is characterized by the fact that it has increased immunoreactivity in comparison with the native sequence. Preferably, the derivative of the epitope according to the invention has an amino acid sequence selected from Seq. No. 16-27.

A further subject of the invention is a way to detect a patient's infection with *Streptococcus agalactiae* characterized by checking the sample taken from the patient for the presence of the protein according to the invention specified above, or the epitope according to the invention specified above, or antibodies specific to this protein or epitope, and at the same time, the presence of this protein, this epitope or such antibodies indicates that the patient is infected with *Streptococcus agalactiae*. Preferably, the test is carried out using known immunochemical methods, especially Western Blotting or ELISA. Equally preferably, human serum is used as the test sample, especially at a dilution of 500-10,000 times.

Following a special execution, the method according to the invention also encompasses detecting the carriage of *Streptococcus agalactiae* strains by the patient studied.

Figure 1:
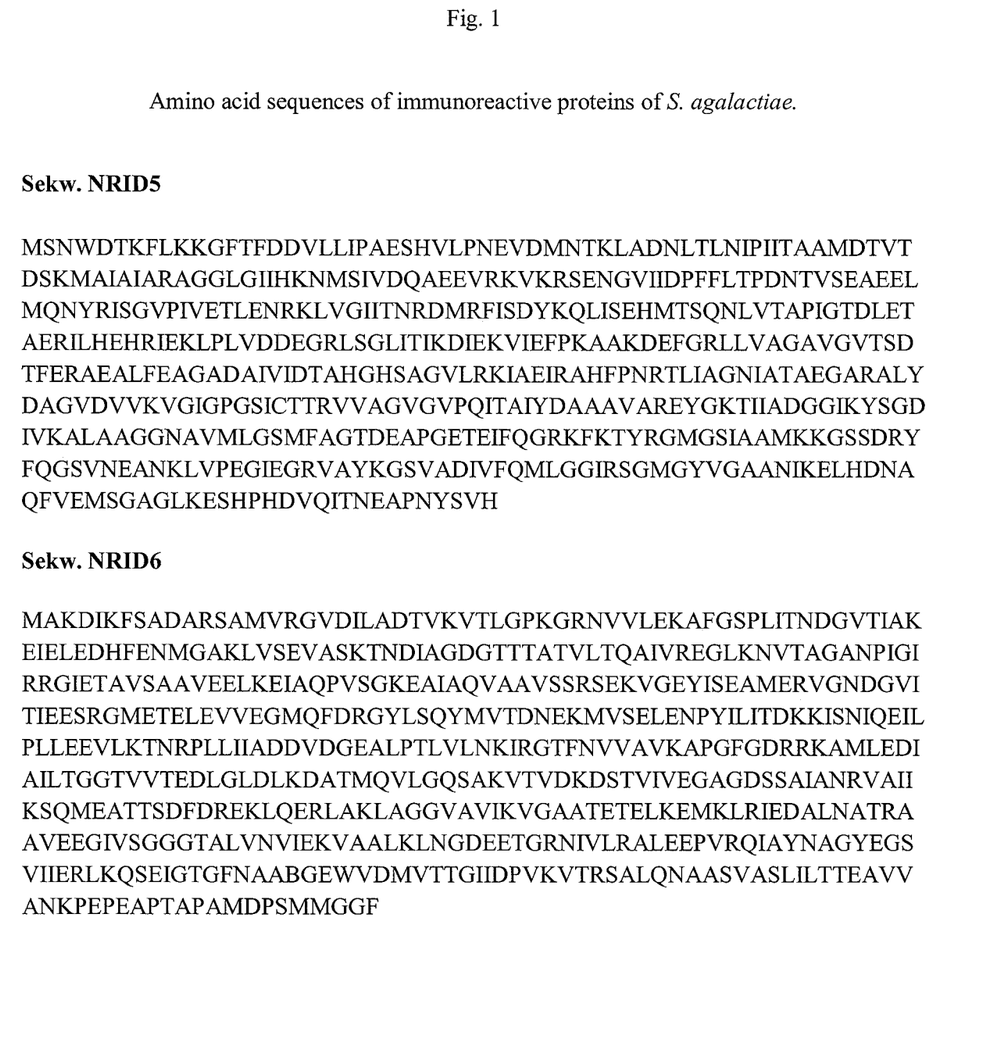
FIG. 1 presents amino acid sequences (SEQ ID NO:1 and SEQ ID NO:2) of immunoreactive proteins of *S. agalactiae*.

The first aspect of the invention are the amino acid sequences of two immunoreactive proteins of pathogenic *Streptococcus agalactiae* strains, meaning NRID5 and NRID6 (Seq. No. 1 and 2, FIG. 1), and also, at least 13 core epitopes comprising the amino acid sequences of known immunoreactive proteins (i.e., NRID2, NRID4, NRID5, and NRID6) derived from clinical strains of *Streptococcus agalactiae* (Table 2). Polypeptide epitopes were consecutively designated as Ep1-Ep13 (Table 1). Here, as a result of modification of core epitopes, derivative epitopes recognized by human antibodies with the highest possible specificity were obtained.

Figure 4:
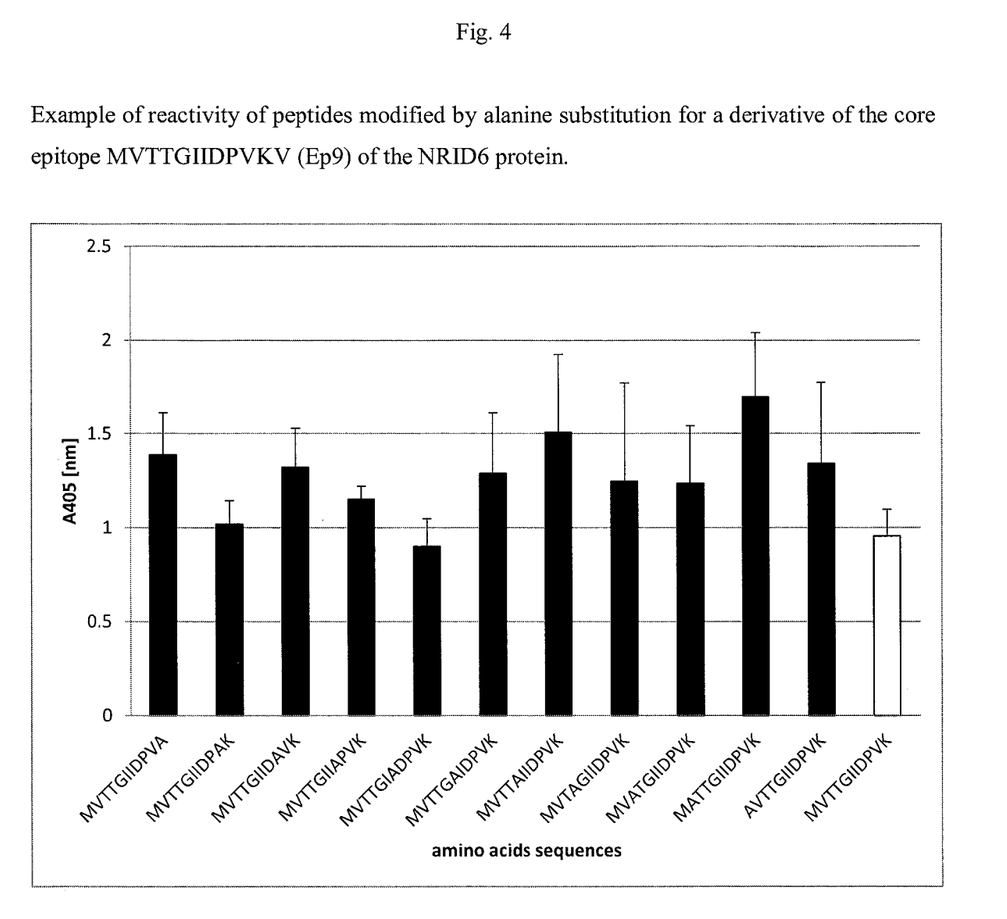
FIG. 4 presents an example of reactivity of peptides (SEQ ID NO:16-27) modified by alanine substitution for a derivative of the core epitope MVTTGIIDPVKV (Ep9) (SEQ ID NO:11) of the NRID6 protein.

Modification consists in truncation of core epitopes from N- and/or C-terminal and/or substitution of one with another amino acid (Table 4, FIG. 4). Unexpectedly, some modifications led to epitopes with higher immunoreactivity than that observed for the natural epitope.

Figure 2:
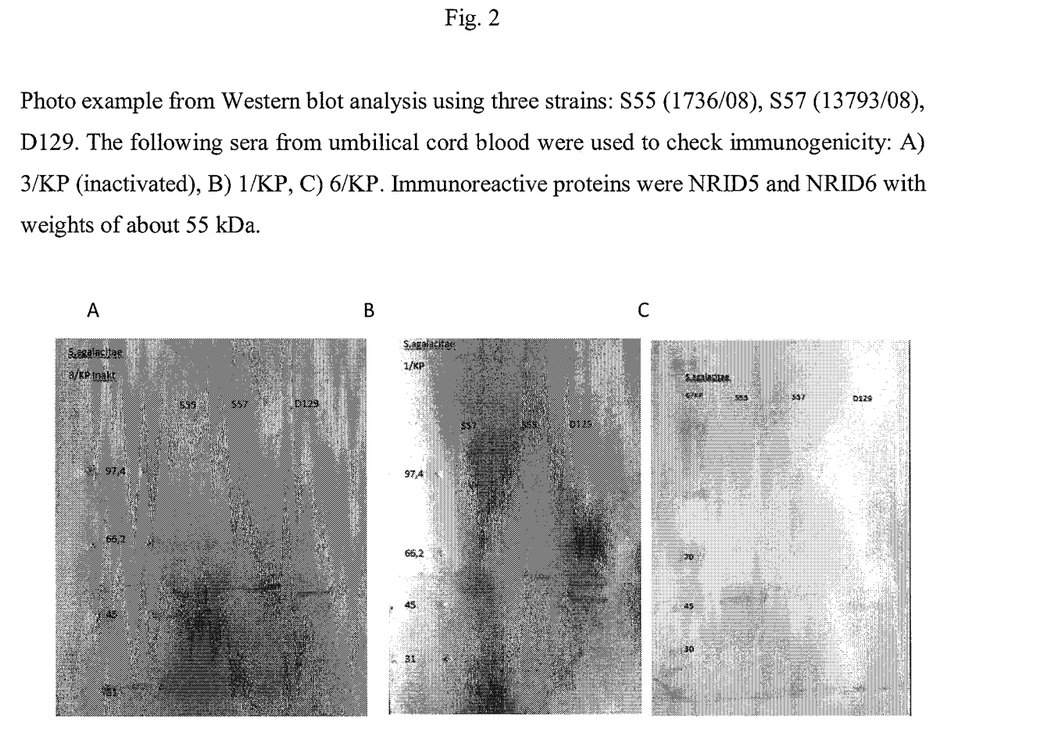
FIG. 2 presents an example picture from Western blot analysis using three strains: S55 (1736/08), S57 (13793/08), D129. The following sera from umbilical cord blood were used to check immunogenicity: A) 3/KP (inactivated), B) 1/KP, C) 6/KP. Immunoreactive proteins were NRID5 and NRID6 with weights of about 55 kDa.

Proteins with sequences marked NRID5 and NRID6, surprisingly, turned out to be highly immunoreactive proteins produced by *Streptococcus agalactiae* strains causing infections in humans. These proteins cause natural immunization which manifests itself in their high immunoreactivity with sera from people infected with GBS and carriers of these bacteria (see Table 3). No similar reactivity was observed in the sera of those uninfected and non-carriers of *Streptococcus agalactiae* (see FIG. 2).

The disclosed method is a solution that enables rapid, sensitive, and specific diagnostics of infection and carriage caused by *Streptococcus agalactiae*. A novel approach in the test developed is the use of epitopes individually and/or in combination which are recognized by human antibodies. Epitopes Ep1-Ep13 and derivatives thereof may then serve to produce highly specific monoclonal antibodies.

The disclosed method involves immunochemical methods, such as e.g., enzyme-linked immunosorbent assay (ELISA).

Preferably executed, the method according to the invention includes the following steps:
   a) 96-well plates are coated with a single epitope and/or a combination of several immunoreactive epitopes which are markers of infections and/or carriage of *Streptococcus agalactiae* strains, preferably at a concentration of 1.0-100 μg/ml in an alkaline-pH buffer. They are subjected to a blocking reaction of free spaces using blocking agent, preferably 0.5-5.0% BSA in phosphate buffer.

b) A reaction is conducted with human serum diluted 100-10000 times, incubated on rocker at 37° C. for an hour, excess of antibodies is washed away using phosphate buffer with detergent, preferably with Tween®-20 at a concentration of 0.01-0.5%.

c) A reaction is carried out with a conjugate of IgG and/or IgM antihuman antibodies with alkaline phosphatase or horseradish peroxidase in a dilution of 500-10000 times on rocker at 37° C. for 1 h. Excess conjugate is washed away with phosphate buffer with Tween®-20.

d) The test is visualized using substrates for alkaline phosphatase or horseradish peroxidase.

Example realizations of the invention have been presented in Figures, in which:

FIG. 5 presents an example of specificity of the derivative of the epitope GQVLAKPGSINPHTKF (Ep. 4) (SEQ ID NO:6) of the NRID4 protein of the sequence KPGSINPH-TKF (amino acids 6-16 of SEQ ID NO:6) assessed in the ELISA test against selected sera: 6/KP—serum from a patient with GBS carriage, GBS 2a—serum from a patient with GBS infection, 13/KP—serum from a non-GBS patient (negative control); GAS—serum from a patient with *S. pyogenes* infection (negative control).

Moreover, the method according to the invention was presented more closely on the examples described below.

EXAMPLE 1

Determination of Immunoreactivity of Epitopes Using PEPSCAN [J. Mark Carter 1996]

A library of several dozen epitopes was obtained as a result of chemical synthesis using polyethylene pins (NCP Block of 96 gears—Mimotopes, cat. no.: MIA10750001) with the application of Fmoc amino acid derivatives according to the procedure:

1. DEPROTECTION—pins we incubated in piperidine solution (PIP) 20% dissolved in dimethylformamide (DMF) for 1 h.
2. RINSING—pins were rinsed once with DMF for 2 min, then four times with methanol (MeOH) for 2 min and dried.
3. COUPLING (amino acid acylation)—pins were activated with DMF for 5 min and then coupled with 60 mM amino acid derivative dissolved in DMF with 65 mM 1-hydroxy-7-azabenzotriazole (HOAt) and 60 mM diisopropylcarbodiimide (DIC) and 50 μM bromophenol blue used as an indicator of the end of the acylation reaction. Aminoacylation was carried out at room temperature (~22° C.) throughout the night or for 4 h in a sealed container, to prevent evaporation of the solution.
4. RINSING
   Variant A: if synthesis was continued, pins were rinsed once with MeOH for 5 min, air-dried for 5 min, and then incubated for 5 min in DMF.
   Variant B: at the end of the synthesis, pins were rinsed once with MeOH for 5 min, air-dried for 5 min, then incubated in DMF for 5 min. After its completion, pins were rinsed twice with MeOH for 2 min and air-dried for 30 min.
5. ELONGATION—consisted in cyclical repetition of stages 1-4.
6. N-ACETYLATION (optional)—acetylation of α-amino groups of the synthesized peptides was carried out in wells of a polyethylene plate using acetylation cocktail (3% acetic anhydride, 0.5% N,N-diisopropyl-ethylamine (DIEA) dissolved in DMF) for 90 min.
7. RINSING—pins were rinsed once with MeOH for 10 min and air-dried for 15 min.
8. SIDE GROUP DEBLOCKING/REMOVAL—blocking side groups were removed from amino acids through 3-4 h of incubation in a bath containing deblocking cocktail (2.5% anisole, 2.5% 1,2-dithioethane in trifluoroacetic acid (TFA))
9. RINSING—pins were rinsed once with MeOH for 10 min and then incubated in acetic acid solution (0.5% acetic acid, 50% MeOH diluted in water) for 60 min. Afterwards, pins were washed twice with MeOH for 2 min and dried throughout the night over desiccant resin.
10. DISRUPTION—pins were placed in a sonicator filled with disruption buffer (1% sodium dodecyl sulfate, 0.1% 2-mercaptoethanol, 0.1 M sodium phosphate; pH 7.2) heated to about 60° C. and sonicated for 10 min (7 kW/25 kHz). Afterwards, pins were removed from the buffer and washed with water heated to 60° C.

Following disruption, pins were stored under anhydrous conditions (e.g., in the presence of a water-absorbing substance or in a desiccator under vacuum conditions) or were employed directly for ELISA.

EXAMPLE 2

ELISA Test [Andersson et al., 1989]

1. Synthetic epitopes on pins were submerged in Tris/HCl blocking buffer with 0.05% Tween®-20 (TBS-T) containing 1% BSA and incubated for 1 h at room temperature.
2. Pins were washed three times with TBS-T buffer for 5 min.
3. After rinsing, pins were incubated in human serum solution diluted 1:1000 for 2 h at room temperature.

4. Pins were washed three times with TBS-T buffer for 5 min.
5. Pins were submerged in a solution containing goat anti-human antibodies coupled to alkaline phosphatase diluted 1:10 000 and incubated for 1 h.
6. Pins were washed three times with TBS-T buffer for 5 min.
7. After washing, pins were submerged in a solution with a substrate for alkaline phosphatase and, for 30 min, a color reaction was induced.
8. Pins were removed and absorbance was read at k=405 nm.

EXAMPLE 3

Synthesis on Wang Resin by Fmoc Applied to Obtain Core Epitopes and their Modified Derivatives [Bachem, 2016]
1. Resin was activated in 20% piperidine solution (PIP) diluted in dimethylformamide (DMF) for 15 min.
2. Resin was rinsed six times in 2 ml of DMF.
3. Additional amino acids were attached to the resin by adding the appropriate number of them, determined according to the formula:

$$M_{compound}=n(\text{active spaces})*2.5\ eq*M_{compound}$$

and 43.7 µl 1-hydroxy-7-azabenzotriazole (HOAt) and 43.9 µl diisopropylcarbodiimide (DIC). Incubation was carried out from 6 to 36 h depending on the nature of the amino acid attached.
4. Resin was rinsed six times in 2 ml of DMF.
5. Stages 2-4 were repeated cyclically until a peptide of the sequence desired was obtained.
6. The peptide was removed from resin using 95% trifluoroacetic acid solution (TFA) dissolved in water.
7. The peptide was precipitated with ether and centrifuged, then dissolved in water and lyophilized.

EXAMPLE 4

ELISA Test for Biotinylated Peptides
1. The well of a 96-well plate was coated with a streptavidin solution diluted in carbonate buffer at a concentration of 1 µg/ml at 4° C. overnight.
2. The wells were rinsed three times (with saline buffered with phosphate with 0.05% Tween®-20 (PBS-T).
3. Biotinylated peptides diluted in carbonate buffer at a concentration of 1 µg/ml were added and incubated for 20 min at room temperature.
4. The wells were rinsed three times with PBS-T.
5. The wells were blocked with 1% BSA solution diluted with PBS-T for 1 h at room temperature.
6. Incubation was carried out with human serum diluted 1:100 for 2 h at room temperature.
7. Unbound antibodies were rinsed three times with PBS-T.
8. Incubation was carried out with a solution of goat anti-human IgM and/or IgG antibodies conjugated with horseradish peroxidase or alkaline phosphatase 1:10, 000 for 1 h at room temperature.
9. Unbound antibodies were rinsed five times with PBS-T.
10. After rinsing, the substrate for horseradish peroxidase or alkaline phosphatase was added to each well and incubated for 30 min in the dark.
11. After the incubation was complete, the reaction was stopped by adding a sulfuric acid solution.
12. The absorbance was measured at a wavelength of 450 nm.

EXAMPLE 5

ELISA Test for Recombinant Protein
1. The well of a 96-well plate was coated with protein dissolved in saline and incubated at 4° C. overnight.
2. The wells were rinsed three times with PBS-T (saline buffered with phosphate with 0.05% Tween®-20.
3. Biotinylated peptides diluted in carbonate buffer at a concentration of 1 µg/ml were added and incubated for 20 min at room temperature.
4. The wells were rinsed three times with PBS-T.
5. The wells were blocked with 1% BSA solution diluted with PBS-T for 1 h at room temperature.
6. Incubation was carried out with human serum diluted 1:100 for 2 h at room temperature.
7. Unbound antibodies were rinsed three times with PBS-T.
8. Incubation was carried out with a solution of goat anti-human IgM and/or IgG antibodies conjugated with horseradish peroxidase or alkaline phosphatase 1:10, 000 for 1 h at room temperature.
9. Unbound antibodies were rinsed five times with PBS-T.
10. After rinsing, the substrate for horseradish peroxidase or alkaline phosphatase was added to each well and incubated for 30 min in the dark.
11. After the incubation was complete, the reaction was stopped by adding a sulfuric acid solution.
12. The absorbance was measured at a wavelength of 450 nm.

RESULTS AND CONCLUSIONS

Figure 3:
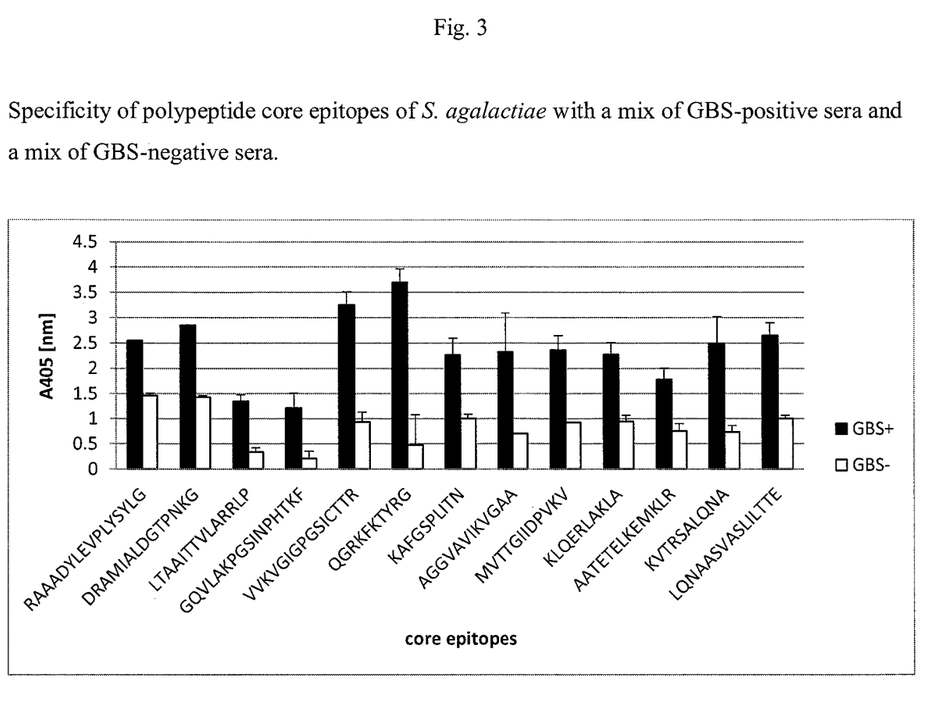
FIG. 3 presents specificity of polypeptide core epitopes of *S. agalactiae* (SEQ ID NO:3-15) with a mix of GBS+ sera and a mix of GBS-sera.
Figure 5A:
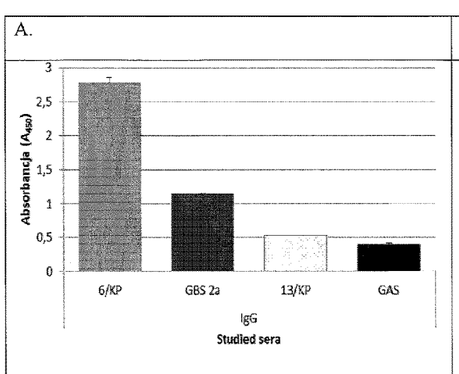
FIG. 5A presents the results obtained for IgG antibodies.
Figure 5B:
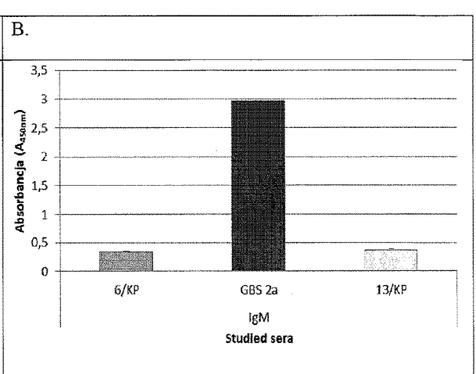
FIG. 5B presents results for IgM antibodies.
Figure 6:
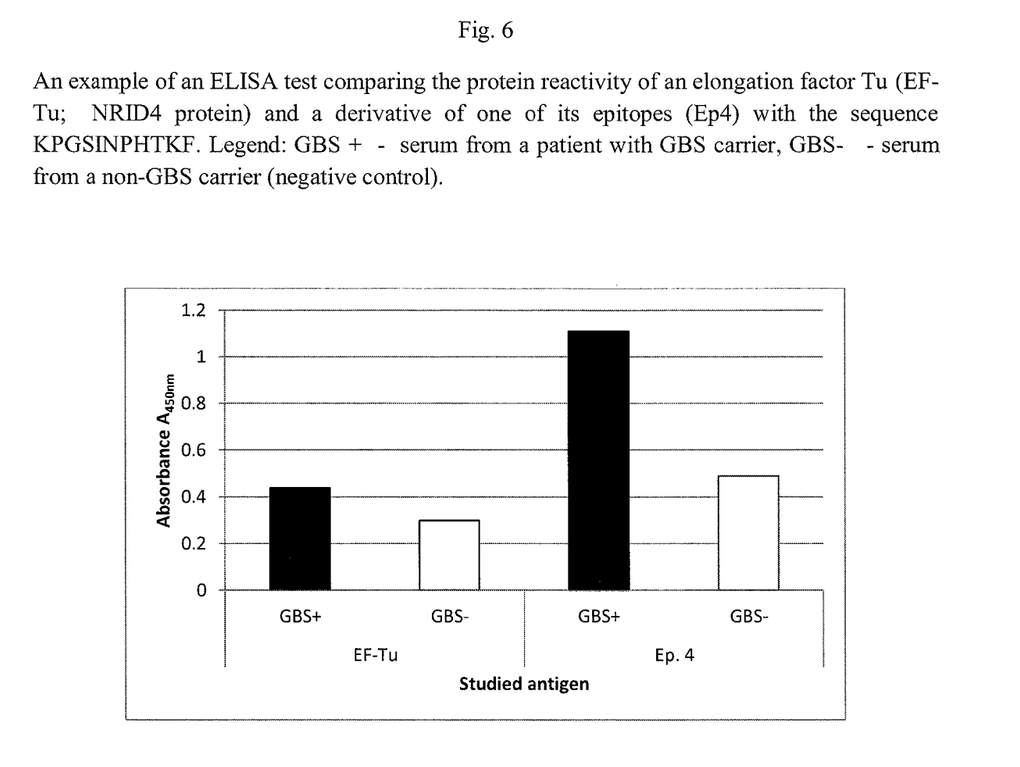
FIG. 6 presents an example ELISA result comparing protein reactivity elongation factor Tu (EF-Tu, NRID4 protein) and the derivative of one of its epitopes (Ep. 4) of the sequence KPGSINPHTKF (amino acids 6-16 of SEQ ID NO:6). Legend: GBS+—serum from an *S. agalactiae* carrier patient, GBS-—serum from a non-GBS patient (negative control), EF-Tu+elongation factor Tu.

As a result of the experiments conducted, 13 core epitopes were identified (Table 1), which were recognized in a highly specific way by human antibodies present in umbilical cord blood serum of GBS-infected patients and/or carriers (GBS+). The reaction was not observed with serum of GBS-negative people (GBS−) (FIG. 3).
Modifications consisting in substituting individual amino acids with, among others, alanine or glycine as well as biotinylation of peptides caused an increase in immunoreactivity ranging from 7 to 80%, which is a non-obvious result (FIG. 4). It was also demonstrated that using two and/or three epitope derivatives in combination test increases the specificity in the reaction with umbilical cord antibodies up to about 40% in comparison to using a single epitope.
Biotinylated epitopes were characterized by high specificity in recognizing infection (high reactivity in the presence of IgM antibodies and average reactivity against IgG antibodies) and carrier state (high reactivity in the presence of IgG antibodies and low reactivity against IgM antibodies). The reaction was not observed with the serum of GBS-negative people (GBS−) or GAS-positive serum, which is a non-obvious result (FIG. 5).
Furthermore, biotinylated epitopes of the immunogenic EF-Tu protein have been demonstrated to more strongly and more specifically recognize anti-GBS antibodies than the whole protein (FIG. 6).

REFERENCES

Andersson G., Ekre H. P., Alm G., Perlmann P. Monoclonal antibody two-site ELISA for human IFN-gamma. Adaptation for determinations in human serum or plasma. J Immunol Methods. 1989; 125:89-96.

Solid phase synthesis Bachem (002363) published by Global Marketing, Bachem Group, February 2016.

Carter J. M. Epitope Mapping of a Protein Using the Geysen (PEPSCAN) Procedure. The Protein Protocols Handbook; 1996, Part V, 581-593.

TABLE 1

Polypeptide core epitopes of *Streptococcus agalactiae*.

| Epitope symbol | Core peptide amino acid sequence | Protein identification no. |
|---|---|---|
| Ep1 | RAAADYLEVPLYSYLG (SEQ ID NO: 3) | NRID2 |
| Ep2 | DRAMIALDGTPNKG (SEQ ID NO: 4) | NRID2 |
| Ep3 | LTAAITTVLARRLP (SEQ ID NO: 5) | NRID4 |
| Ep4 | GQVLAKPGSINPHTKF (SEQ ID NO: 6) | NRID4 |
| Ep5 | VVKVGIGPGSICTTR (SEQ ID NO: 7) | NRID5 |
| Ep6 | QGRKFKTYRG (SEQ ID NO: 8) | NRID5 |
| Ep7 | KAFGSPLITN (SEQ ID NO: 9) | NRID6 |
| Ep8 | AGGVAVIKVGAA (SEQ ID NO: 10) | NRID6 |
| Ep9 | MVTTGLIDPVKV (SEQ ID NO: 11) | NRID6 |
| Ep10 | KLQERLAKLA (SEQ ID NO: 12) | NRID6 |
| Ep11 | AATETELKEMKLR (SEQ ID NO: 13) | NRID6 |
| Ep12 | KVTRSALQNA (SEQ ID NO: 14) | NRID6 |
| Ep13 | LQNAASVASLILTTE (SEQ ID NO: 15) | NRID6 |

TABLE 2

Characteristics of clinical strains of bacteria from the species *S. agalactiae*.

| Strain No | Strain name | Clinical material | Patient/ diagnosis | Serotype | Alp family genes | Resistance phenotype | ermB gene | mefA/E gene |
|---|---|---|---|---|---|---|---|---|
| 1 | 1736/08 | urine | newborn UTI* | V | alp2 | cMLS$_B$ | ermB | — |
| 2 | D129 | urine | woman UTI* | III | rib | — | — | — |
| 3 | D437 | urine | woman UTI* | Ib | epsilon | — | — | — |
| 4 | D280 | urine | man UTI* | Ia | epsilon | — | — | — |
| 5 | D481 | urine | woman UTI* | V | rib | — | — | — |
| 6 | G413 | urine | woman UTI* | V | alp2 | — | — | — |
| 7 | G408 | urine | woman UTI* | Ib | epsilon | — | — | — |
| 8 | G437 | urine | woman UTI* | III | rib | — | — | — |
| 9 | G361 | urine | man UTI* | IV | epsilon | — | — | — |
| 10 | 286378 | urine | man UTI* | II | rib | cMLS$_B$ | ermB | — |
| 11 | 300666 | urine | man UTI* | V | alp2 | iMLS$_B$ | — | — |
| 12 | 305139 | urine | newborn UTI* | II | bca | — | — | — |
| 13 | 306723 | urine | newborn UTI* | III | alp2 | — | — | — |
| 14 | 13793/08 | urine | newborn UTI* | V | alp2 | cMLS$_B$ | ermB | — |
| 15 | 13723/07 | urine | newborn UTI* | III | rib | cMLS$_B$ | ermB | — |
| 16 | 2992/08 | urine | newborn UTI* | V | rib | — | — | — |
| 17 | 5303/08 | urine | newborn UTI* | Ia | epsilon | — | — | — |
| 18 | PP4 | vaginal swab | woman carriage | n/a | alp2/3 | — | — | — |
| 19 | PP6 | vaginal swab | woman carriage | n/a | alp2/3 | — | — | — |
| 20 | PP7 | vaginal swab | woman carriage | n/a | bd | — | — | — |
| 21 | PP8 | vaginal swab | woman carriage | n/a | alp2/3 | — | — | — |

TABLE 2-continued

Characteristics of clinical strains of bacteria from the species *S. agalactiae*.

| Strain No | Strain name | Clinical material | Patient/diagnosis | Serotype | Alp family genes | Resistance phenotype | ermB gene | mefA/E gene |
|---|---|---|---|---|---|---|---|---|
| 22 | PP9 | vaginal swab | woman carriage | n/a | rib | — | — | — |
| 23 | NPP1 | vaginal swab | woman carriage | n/a | n/a | — | — | — |
| 24 | GAS1 | pharyngeal swab | child tonsillitis | n/a | n/a | — | — | — |
| 25 | GBS1 | pharyngeal swab | child tonsil infection | n/a | alp2/3 | — | — | — |
| 26 | GBS2 | wound swab | woman necrotizing fasciitis | n/a | n/a | — | — | — |
| 27 | 2337/08 | mouth swab | newborn colonization | Ia | epsilon | — | — | — |
| 28 | CM47 | blood | newborn EOD** | II | rib | ckMLS$_B$ | ermB | — |
| 29 | 13793/08 | blood | newborn EOD** | V | alp2 | cMLS$_B$ | ermB | — |
| 30 | 2992/08 | urine | newborn UTI* | V | rib | — | — | — |

*UTI—urinary tract infection (*S. agalactiae* >10$^5$ CFU/ml); **EOD—early onset disease; n/a—not available; "—"—none; cMLS$_B$—constitutive resistance to macrolides, lincosamides, streptogramin B; iMLS$_B$—inducible resistance to macrolides, lincosamides, streptogramin B.

TABLE 3

List of GBS-positive and GBS-negative sera employed to evaluate the specificity of immunoreactive proteins of *S. agalactiae* and their epitopes in immunochemical tests.

| Venous blood | Umbilical cord blood |
|---|---|
| GBS-positive sera: | |
| SK1, SK2, PP4, PP6, PP7, PP8, PPG, NPP1, GBS1, GBS2a, GBS2b, PP9, SB3b, SB4b, PP7, 28/3, 14/3, 10/3, 3/3, 42/3 | 1/KP, 2/KP, 3/KP, 4/KP, 5/KP, 6/KP, 8/KP, 10/KP, 14/KP, 15/KP, 16/KP |
| GBS-negative sera: | |
| SK8, SB7, SB8, SB9, SB1a, SB1b, SB3a, 5/3, 13/3, 22/3, 34/3 | 12/KP, 13/KP, 24/KP, 28/KP, 29/KP |

TABLE 4

Percent increase in immunoreactivity of derivatives of the epitope MVTTGHDPVK against GBS-positive serum, obtained as a result of alanine substitution of subsequent amino acids.

| Peptide | Average absorbance (A405 nm GBS+) | % increase in reactivity compared to the starting sequence (MVTTGIIDPVK) |
|---|---|---|
| MVT1-GIIDPVA (SEQ ID NO: 16) | 1.38510001 | an increase of 45% |
| MVTTGIIDPAK (SEQ ID NO: 17) | 1.01940002 | an increase of 7% |
| MVTTGIIDAVK (SEQ ID NO: 18) | 1.32013333 | an increase of 38% |
| MVTTGIIAPVK (SEQ ID NO: 19) | 1.15009999 | an increase of 21% |
| MVTTGIADPVK (SEQ ID NO: 20) | 0.89886667 | a decrease of 6% |
| MVTTGAIDPVK (SEQ ID NO: 21) | 1.28863335 | an increase of 35% |
| MVTTAIIDPVK (SEQ ID NO: 22) | 1.50660002 | an increase of 58% |

TABLE 4 -continued

Percent increase in immunoreactivity of derivatives of the epitope MVTTGHDPVK against GBS-positive serum, obtained as a result of alanine substitution of subsequent amino acids.

| Peptide | Average absorbance (A405 nm GBS+) | % increase in reactivity compared to the starting sequence (MVTTGIIDPVK) |
|---|---|---|
| MVTAGIIDPVK (SEQ ID NO: 23) | 1.24636666 | an increase of 31% |
| MVATGIIDPVK (SEQ ID NO: 24) | 1.2343667 | an increase of 30% |
| MATTGIIDPVK (SEQ ID NO: 25) | 1.69836664 | an increase of 78% |
| AVTTGIIDPVK (SEQ ID NO: 26) | 1.34063331 | an increase of 40% |
| MVTTGIIDPVK (SEQ ID NO: 27) | 0.95466667 | |

The invention claimed is:

1. A plate for an ELISA specific for infectious *Streptococcus agalactiae* comprising an isolated peptide in the well of the plate, wherein the peptide consists of an amino acid sequence selected from SEQ ID NO:7 through SEQ ID NO:27.

2. The plate for an ELISA according to claim 1, wherein the peptide consists of an amino acid sequence selected from SEQ ID NO:7 through SEQ ID NO: 15.

3. The plate for an ELISA according to claim 2, wherein the peptide consists of an amino acid sequence selected from SEQ ID NO:16 through SEQ ID NO:27.

4. A method to detect a patient's infection with a *Streptococcus agalactiae* strain comprising contacting a sample taken from the patient with the ELISA plate of claim 1 and detecting the interaction of antibodies in the sample with the peptide on the ELISA plate, wherein the presence of said antibodies indicates infection of the patient with a *Streptococcus agalactiae* strain.

5. A method to detect a patient's infection with a *Streptococcus agalactiae* strain comprising contacting a sample taken from the patient with a protein or peptide consisting of an amino acid sequence selected from SEQ ID NO:7 through SEQ ID NO:27 and detecting the interaction of antibodies in the sample with the protein or peptide, wherein the presence of said antibodies indicates infection of the patient with a *Streptococcus agalactiae* strain.

6. The method of claim 5, wherein the method is a Western Blot.

7. The method of claim 4, wherein the patient is a *Streptococcus agalactiae* carrier.

8. The method of claim 5, wherein the patient is a *Streptococcus agalactiae* carrier.

* * * * *